United States Patent [19]

Tsuji et al.

[11] Patent Number: 4,851,241
[45] Date of Patent: Jul. 25, 1989

[54] PROCESS FOR TREATING MEAT WITH RAW SOY SAUCE

[75] Inventors: Ryohei Tsuji, Noda; Mitsuo Takahashi, Nagareyama, both of Japan

[73] Assignee: Kikkoman Corporation, Noda, Japan

[21] Appl. No.: 206,923

[22] Filed: Jun. 10, 1988

Related U.S. Application Data

[63] Continuation of Ser. No. 862,640, May 13, 1986, abandoned.

[30] Foreign Application Priority Data

May 27, 1985 [JP] Japan ................... 60-112291

[51] Int. Cl.4 .................. A23L 1/314; A23L 1/318
[52] U.S. Cl. .......................... 426/56; 426/58; 426/59; 426/281; 426/641; 426/646
[58] Field of Search ............ 426/56, 58, 59, 281, 426/641, 644, 646, 652

[56] References Cited

U.S. PATENT DOCUMENTS 3,216,826 11/1965 Wattenbarger ................ 426/58

FOREIGN PATENT DOCUMENTS 15422 10/1960 Japan .
6794 5/1964 Japan .
17891 4/1981 Japan .

Primary Examiner—Arthur L. Corbin
Attorney, Agent, or Firm—Banner, Birch, McKie & Beckett

[57] ABSTRACT

A process for treating a meat by bringing the meat into contact wiht a raw soy sauce.

4 Claims, No Drawings

PROCESS FOR TREATING MEAT WITH RAW SOY SAUCE

This application is a continuation of application Ser. No. 862,640, filed May 13, 1986, now abandoned.

BACKGROUND OF THE INVENTION

1. Field of the Invention

This invention relates to a process for tenderizing and flavoring a meat such as beef, mutton, port, or poultry by bringing the meat into contact with a raw soy sauce.

2. Description of the Prior Art

Up the present, many attempts have already been made to tenderize the meat by various enzymes. The enzymes now being used worldwidely in meat tenderizing agents are cysteine proteinase of the vegetable origin. Of these enzymes, particularly in general use in papain, though other proteases such as bromelain (bromelin) and ficin are also used. In applying these enzymes to the tenderization of meats, the procedures generally employed as dusting a lump of meat with a powdered enzyme; dipping a lump of meat into an enzyme solution; puncture treatment of a lump of meat; and injecting an enzyme solution into the blood vessel before slaughtering the animal.

An important factor for the tenderization of meat with a protease is the appropriate degradation of connective tissue such as collagen, elastin, and reticulin; particularly, the degradation of collagen which occupies 80% of the connective tissue is a key factor, because it is generally believed that enzymes conventionally used in meat tenderization, such as papain, bromelain, and ficin have no collagenase activity. In fact, when being acted upon by these enzymes, the meat becomes powdery on the surface, or becomes stinking. After all, conventional meat tenderizing agents have a disadvantage in that they act on myofibrils in preference to connective tissue, thus rendering the meat unsuitable for a tasty food.

SUMMARY OF THE INVENTION

The present inventors found that when a meat is treated with a raw soy sauce, the connective tissue such as collagen and elastin react intensively and myofibrils react moderately to yield a tenderized meat excellent in tenderness, easy to bite, and excellent in texture, without showing any powdery or roughened surface. Based on this finding, the present invention has been accomplished. This invention, therefore, provides a process of treating a meat characterized by bringing the meat into contact with a raw soy sauce.

DETAILED DESCRIPTION OF THE INVENTION

The meat suitable for the treatment according to this invention includes beef (and veal), mutton (and lamb), pork, and poultry.

The raw soy sauces suitable for use in the present process are those which retain the flavor of soy sauce and various enzymatic activites acquired in brewing the soy sauce, such as, for example, a raw soy sauce obtained by pressing the soy "moromi" (soy mash) after ripening, a clarified raw soy sauce obtained by removing scums and sediments after the raw soy sauce has been left standing for some time, and adjusted raw soy sauce obtained by adding water and sodium chloride to the clarified raw soy sauce.

The meat to be treated is cut to suitable sizes such as lump or smaller pieces or is changed into chopped meat according to the purpose of use. The meat as such or kept at a suitable temperature (0° to 30° C.) is brought into contact with the raw soy sauce in a proper amount depending upon the toughness of meat. The contact is effected by injecting the raw soy sauce into the meat by a suitable device, or by dipping, spraying or coating the raw soy sauce on the meat. The injection is preferred for the purpose of uniform tenderization. These methods of treatment may be used each alone or in combinations. The meat is held in contact with the proper amount of raw soy sauce for a predetermined period of time to allow the reaction to proceed. The amount of raw soy sauce and the reaction time are selected depending on the enzymatic activities of the raw soy sauce and temperature of the meat. Before use, the raw soy sauce can be adjusted, if necessary, in sodium chloride content, for example, by means of ion-exchange resins, in nitrogen and alcohol content, and in pH.

A typical example is described below to illustrate the procedure of brewing, properties, and constituents of raw soy sauce.

The soy sauce is brewed generally by the following procedure.

Whole soybeans are steeped in water and cooked or, alternatively, defatted soybeans are sprinkled with water and cooked. On the other hand, wheat is roasted and crushed. The cooked whole soybeans or cooked defatted soybeans and the cooked crushed wheat are blended. A strain belonging to the genus Aspergillus (koji-mold) is added to the blend and subjected to koji making to yield soy sauce koji. The soy sauce koji together with a sodium chloride solution is charged into a tank to make moromi (mash) which is allowed to ferment, producing ripened moromi. The ripened moromi is removed of lees by pressing to obtain a liquor which is called raw soy sauce. "Koikuchi" soy sauce (ordinary soy sauce) is obtained by the heat sterilization (pasteurization) of the raw soy sauce.

An example of the procedure of soy sauce brewing is described below.

One hundred kilograms of defatted soybeans which have been denatured by cooking and 105 kg of wheat which have been roasted and crushed are blended. The resulting blend is inoculated with a koji-mold and the koji making is carried out for 42 hours under aeration to yield soy sauce koji. To this koji, is added 360 liters of a sodium chloride solution containing 90 kg of sodium chloride. The resulting mixture is charged into a closed-type tank of 600 liters in volume. In 60 days of mashing after the charging, yeast is added to the mashing mixture and mashing is continued for 6 months under customarily controlled conditions to produce ripened mash. The ripened mash is pressed in a customary manner to obtain a raw soy sauce.

The raw soy sauce contains many kinds of microorganisms (lactic acid bacteria, yeast, and others) and enzymes (protease, amylase, phosphatase, etc.). Examples of enzymatic activites are shown in Table 1. The raw soy sauce has generally a sodium chloride content of 12–17%, a total nitrogen content of 1–3%, an alcohol content of 1–5%, and a pH value of 4–5.5.

When a meat is brought into contact with raw soy sauce, the meat undergoes enzymatic reactions caused by various enzymes in the raw soy sauce, resulting in uniform tenderization of meat tissues. There is thus produced a meat having desirable tenderness and flavors imparted by the raw soy sauce. The meat treated according to the present invention can be used directly, or after preservation in a freezer or refrigerator, in cooking meat dishes such as meat steaks or as raw material in processing into meat ham or sausage.

In carrying out the present process, the raw soy sauce can be used jointly with conventional meat tenderizing agents such as papain, bromelain, and ficin. Further, if necessary, the raw soy sauce can be admixed with preservatives such as sodium salt, methylester, or propyl ester of benzoic acid; stabilizers such as calcium chloride; seasonings and flavorings such as ginger, black pepper, nutmeg, and garlic. The resulting flavored raw soy sauce can be used as a flavoring and tenderizing agent for meat.

The invention is illustrated below with reference to experiment examples.

EXPERIMENT EXAMPLE 1

The results of assay for proteolytic activities of raw soy sauce and papain (mfd. by Wako Junyaku Kogyo Co.; Activity=1:350) were as shown in Table 1.

TABLE 1

|  | Proteinase activity | Collagenase activity | Elastase activity |
|---|---|---|---|
| Papain (Unit/mg) | 15.4 | 0 | 3.60 |
| Raw soy sauce (Unit/ml) | 54.4 | 3.09 | 6.07 |

Note 1:
Before use, papain was activated with 5 mM cysteine -2 mM EDTA for the assay of proteinase activity and with 10 mM BAL (2,3-dimercapto-propanol) for the assay of collagenase activity and elastase activity. The raw soy sauce contained 16.85% of sodium chloride, 1.572% of total nitrogen (T.N.), and 2.60% of ethanol (Alc.). Before use, the raw soy sauce dialyzed overnight was diluted 4-fold with water. Note 2:
The proteinase activity was assayed, using 1% hemoglobin as substrate, by the method of Arnon for papain and by the method of Anson-Hagiwara for raw soy sauce. The collagenase activity was assayed by the method of Nagai et al. using a synthetic substrate, Z-Gly. Pro.Leu.Gly.Prop.H$_2$O.AC-OET (mfd. by Protein Research Foundation). The elastase activity was assayed by the method of Bieth et al., using Suc-(Ala)$_3$-pNA (mfd. by Protein Research Foundation) as substrate.

As shown in Table 1, it was found that papin does not degradate collagen as generally known, whereas the raw soy sauce contains as enzyme which acts specifically on collagen.

EXPERIMENT EXAMPLE 2

A cut of rump of a castrated Holstein was aged at 0° C. for 14 days and used as meat sample. A slice of meat sample, 1 cm in thickness, was brought to an internal temperature of 25° C. The same raw soy sauce as used in Experiment Example 1 was uniformly injected into the slice of meat to a depth of 0.5 cm at the spots distributed over the surface at a distance of 1 cm between adjacent spots. The total amount of injected raw soy sauce was 2% of the weight of meat. The injected meat was kept for the length of time as shown in Table 2 to allow the reaction to proceed.

The treated meat was cooked in water at 90° C. for 20 minutes and the tenderizing ability was evaluated by means of a rheometer (R-UD IV of Fuji Rika Kogyo Co.). The results were as shown in Table 2.

TABLE 2

| Reaction time (min.) | Item of test | |
|---|---|---|
|  | Toughness (kg W) | Elasticity (%) |
| 0 (control) | 1.077 ± 0.060 | 57.9 ± 6.5 |
| 15 | 1.050 ± 0.087 | 52.0 ± 4.5 |
| 30 | 0.973 ± 0.104 | 49.1 ± 6.0 |
| 60 | 0.892 ± 0.087 | 44.3 ± 3.4 |

Note:
The tenderizing ability was evaluated by compressing the meat at various spots with a plunger, 4 mm in diameter, to 70% of the initial thickness. The compression test was conducted twice in succession at each spot of the meat surface. The toughness and elasticity were calculated from the chart of test by the following equations:

$$\text{Toughness} = \text{Height of the peak of first compression}$$

$$\text{Elasticity} = \frac{\text{Time elapsed before the peak of second compression is reached}}{\text{Time elapsed before the peak of first compression is reached}} \times 100$$

As is apparent from Table 2, the toughness and elasticity declined with the time of reaction with the raw soy sauce.

The invention is further illustrated below in detail with reference to examples.

EXAMPLE 1

A chopped beef (from a castrated Holstein ripened at 0° C. for 14 days), 3 cm in thickness, was injected at a depth of 1.5 cm at the spots distributed over the surface at a distance of 1 cm between adjacent spots with a raw soy sauce in an amount of 10% of the weight of meat, said raw soy sauce having a proteinase activity of 54.4 Unit/ml, a collagenase activity of 3.09 Unit/ml, and an elastase activity of 6.07 Unit/ml. The meat was allowed to react at 30° C. for 30 minutes to yield a beef having a desirable flavor.

Another chopped beef was treated in the same manner as described above, except that a pasteurized soy sauce was used in place of the raw soy sauce. The treated beef was used as control.

Both treated beef samples were cooked on a hot plate at a surface temperature of 180°–200° C. until the internal temperature had reached 65° C. The cooked beef samples were subjected to sensory panel test. The results obtained were as shown in Table 3.

TABLE 3

|  | Control (treated with pasteurized soy sauce) | This invention (treated with raw soy sauce) |
|---|---|---|
| Tenderness | 2.58 ± 0.55 | **4.00 ± 0.59 |
| Easiness of biting off powdery or roughened surface | 2.64 ± 0.80 | **3.72 ± 0.75 |
|  | 1.47 ± 0.85 | 1.78 ± 0.65 |
| Total evaluation | 2.94 ± 0.73 | *3.61 ± 0.78 |

Note:
The sensory panel test was conducted by 18 skilled members according to the following rating system and the results were expressed in average rating value together with standard deviation. ** means significant at 1% level of significance and * means significant at 5% level of significance.

|   | 1 | 2 | 3 | 4 | 5 |
|---|---|---|---|---|---|
| Tenderness: | very tough | tough | normal | tender | very tender |
| Easiness of bitting-off: | very difficult | difficult | normal | easy | very easy |
| Powdery or roughened surface: | none | | powdery | | very powdery |
| Total evaluation: | very undesirable | undesirable | normal | desirable | very desirable |

As shown in Table 3, the beef treated with a raw soy sauce according to this invention was excellent in tenderness and easiness of bitting-off without showing powdery or roughened surface and was desirable in the total evaluation.

EXAMPLE 2

The meat of rump of a castrated Holstein, which has been aged at 0° C. for 14 days after slaughtering and preserved in a freezer at −20° C., was cut perpendicularly to myofibrils to a piece of 1 cm in thickness. The cut meat was punctured with a needlelike tool all over the surface at an interval of 1 cm between adjacent punctures and then preheated at 25° C. for 30 minutes. The preheated meat was dipped in a raw soy sauce preheated at 25° C. to undergo enzymatic reaction. There was obtained a meat with a desirable flavor.

The treated meat and a control meat (a meat treated in the same manner as described above, except that pasteurized soy sauce was used in place of the raw soy sauce) were cooked together in a frying-pan. Both cooked pieces of meat were subjected to sensory panel tests. The results obtained were as shown in Table 4.

TABLE 4

|   | Meat of this invention | Proportion of panel members in favor of meat of this invention (%) |
|---|---|---|
| Tenderness | +1.2 ± 0.3 | 91 |
| Easiness of bitting-off | +1.2 ± 0.2 | 91 |
| Total evaluation | +1.5 ± 0.3 | 100 |

Note:
The sensory panel tests were conducted by a panel of 8 skilled members. Tenderness, easiness of bitting-off, and total evaluation were evaluated in terms of rating value ranging from -3 to +3, assuming that the rating values for the control to be zero. The plus sign means "desirable" and the minus sign means "undesirable". The results were expressed in average value together with standard deviation.

As shown in Table 4, the meat sample treated with the raw soy sauce by puncturing and dipping showed superiority to the control sample in tenderness and easiness of bitting-off. The meat treated according to this invention was evaluated good by all of the panel members.

EXAMPLE 3

A raw soy sauce was desalted with an ion exchange resin and concentrated to yield a desalted raw soy sauce having a sodium chloride content of 13%, total nitrogen content of 2.15%, alcohol content of 3.3%, and a proteinase activity of 54.4 Unit/ml. To the desalted raw soy sauce, were added 0.3% of papain (Wako Junyaku Kogyo Co.; Activity=1:350) and $1.0 \times 10^{-2}$ M of calcium chloride. After adjusting pH to 5.0, there was obtained a seasoning solution for tenderizing meat.

A piece of beef (from a castrated Holstein aged at 0° C. for 14 days), 3 cm in thickness was punctured with a needle-like tool all over the surface at a regular 1 cm interval between adjacent punctures and dipped in said seasoning solution at 20° C. for 30 minutes to yield a treated meat with a desirable flavor. A control beef sample was obtained by treating another piece of beef with a pasteurized soy sauce.

Both of the beef treated according to this invention and the control were cooked on a hot plate at a surface temperature of 180°-200° C. until the internal temperature had reached 65° C., and then subjected to sensory panel tests. The results obtained were as shown in Table 5.

TABLE 5

|   | Control (treated with pasteurized soy sauce) | This invention (treated with raw soy sauce) |
|---|---|---|
| Tenderness | 3.23 ± 0.73 | *3.70 ± 0.59 |
| Easiness to bite off | 2.93 ± 0.98 | *3.65 ± 0.81 |
| Powdery or roughened surface | 1.50 ± 0.83 | 1.33 ± 0.57 |
| Total evaluation | 3.08 ± 0.83 | *3.80 ± 0.59 |

Note:
The sensory panel tests were conducted in the same manner as in Example 1, except that the number of skilled panel members was 20.

As shown in Table 5, the beef treated with a raw soy sauce according to this invention was excellent in tenderness and easiness of bitting-off without showing powdery or roughened surface and was desirable in the total evaluation.

According to this invention, a meat such as beef, mutton, pork, or poultry is treated with a raw soy sauce retaining the flavor of soy sauce and the well-balanced balanced activities of proteinase, collagenase, and elastase, which were acquired during the brewing. The treatment according to this invention eliminates the powdery surface and other disadvantages observed when conventional tenderizing agents such as papain, bromelain, and ficin are used. The raw soy sauce acts intensively on the connective tissue of the meat, which is composed of such proteins as collagen, elastin, and the like, and moderately also on myofibrils, thus yielding a meat which has a desirable flavor imparted by the soy sauce and is excellent in tenderness, easiness of bitting-off, and total evaluation, being free of powdery or roughened appearance. The process of this invention, therefore, will contribute much to the people's diet.

What is claimed is:

1. A process for tenderizing meat which consists essentially of subjecting the meat to at least one contact treatment with a raw soy sauce consisting essentially of liquid obtained by pressing a ripened moromi, said contact treatment selected from the group consisting of injecting said raw soy sauce into the meat, and dipping the meat into said raw soy sauce, said contact treatment being sufficient to tenderize the meat.

2. A process for tenderizing a meat according to claim 1, wherein the meat is at least one member selected from the group consisting of beef, mutton, pork, and poultry.

3. A process for tenderizing a meat according to claim 1, wherein the raw soy sauce further contains at least one member selected from the group consisting of papain, ficin, and bromelain.

4. A process for tenderizing a meat according to claim 1, wherein the raw soy sauce further contains at least one member selected from the group consisting of stabilizer, preservatives, seasonings, and flavorings.

* * * * *